(12) United States Patent
Carver

(10) Patent No.: US 10,285,141 B1
(45) Date of Patent: May 7, 2019

(54) DATA SYNCHRONIZATION ACROSS MULTIPLE SENSORS

(71) Applicant: SAFECO INSURANCE COMPANY OF AMERICA, Seattle, WA (US)

(72) Inventor: Christopher J. Carver, Bainbridge Island, WA (US)

(73) Assignee: SAFECO INSURANCE COMPANY OF AMERICA, Seattle, WA (US)

( * ) Notice: Subject to any disclaimer, the term of this patent is extended or adjusted under 35 U.S.C. 154(b) by 1388 days.

(21) Appl. No.: 13/622,793

(22) Filed: Sep. 19, 2012

(51) Int. Cl.
  *H04W 56/00* (2009.01)
  *H04L 7/00* (2006.01)
  *A61B 5/00* (2006.01)
(52) U.S. Cl.
  CPC ........... *H04W 56/00* (2013.01); *A61B 5/0015* (2013.01); *H04L 7/00* (2013.01)
(58) Field of Classification Search
  CPC ..................................................... G06F 3/011
  USPC ......................................................... 702/150
  See application file for complete search history.

(56) References Cited

U.S. PATENT DOCUMENTS

| | | | |
|---|---|---|---|
| 5,883,593 A | 3/1999 | Chamouard et al. | |
| 5,900,909 A * | 5/1999 | Parulski ................ | H04N 1/2112 348/231.6 |
| 6,199,170 B1 | 3/2001 | Dietrich | |
| 6,759,979 B2 * | 7/2004 | Vashisth ................ | G01C 11/02 342/357.31 |
| 6,882,912 B2 * | 4/2005 | DiLodovico ........... | G08G 1/164 701/301 |
| 7,050,928 B2 * | 5/2006 | Krumm .......................... | 702/150 |
| 7,190,946 B2 | 3/2007 | Mazzara, Jr. et al. | |
| 7,623,961 B2 | 11/2009 | Van Den Broeck | |
| 7,660,203 B2 * | 2/2010 | Barakat et al. .................. | 367/76 |
| 8,050,881 B1 * | 11/2011 | Yeung .................. | A61B 5/0024 370/503 |

(Continued)

FOREIGN PATENT DOCUMENTS

WO  WO-2011/092167 A1  8/2011

OTHER PUBLICATIONS

Tu, K. Y., et al., "Clock Synchronization Using GPS/GLONASS Carrier Phase," *Proceedings of the 32nd Annual Precise Time and Time Interval (PTTI) Meeting*, Nov. 28-30, 2000, pp. 171-180 Chicago, retrieved from <http://www.dtic.mil/cgi-bin/GetTRDoc?Location=U2&doc=GetTRDoc.pdf&AD=ADA485817> on Jun. 17, 2013.

(Continued)

*Primary Examiner* — Alexander Satanovsky
*Assistant Examiner* — Lina M Cordero
(74) *Attorney, Agent, or Firm* — Alston & Bird LLP

(57) ABSTRACT

Various embodiments of the present invention provide methods, systems, apparatus, and computer program products for synchronizing data across at least two sensors. In one embodiment, first sensor data, which includes a universal time stamp from a universal time source, is recorded from at least one first sensor and second sensor data, which does not include a universal time stamp from a universal time source, is recorded from at least one second sensor. The first sensor data is correlated with the second sensor data, and a universal time that corresponds with the data from the second sensor is determined at least in part based on the correlation between the first sensor data and the second sensor data.

9 Claims, 7 Drawing Sheets

(56) References Cited

U.S. PATENT DOCUMENTS

| | | | | |
|---|---|---|---|---|
| 8,213,749 | B2* | 7/2012 | Di Bernardo | G01C 11/02 340/995.1 |
| 8,390,474 | B2* | 3/2013 | Yi | G07C 5/008 340/870.02 |
| 2003/0109264 | A1* | 6/2003 | Syrjarinne | H04W 64/00 455/456.1 |
| 2005/0068293 | A1* | 3/2005 | Satoh | G01C 9/00 345/158 |
| 2005/0273258 | A1* | 12/2005 | MacNeille | G01S 5/0072 701/300 |
| 2007/0025484 | A1* | 2/2007 | Laine et al. | 375/355 |
| 2007/0182623 | A1* | 8/2007 | Zeng | G01S 7/4026 342/174 |
| 2007/0273842 | A1* | 11/2007 | Morrison | G03B 21/14 353/97 |
| 2008/0224924 | A1* | 9/2008 | Lethbridge | G01S 19/05 342/357.29 |
| 2009/0237298 | A1 | 9/2009 | Vollath et al. | |
| 2010/0109944 | A1 | 5/2010 | Whitehead et al. | |
| 2010/0318257 | A1* | 12/2010 | Kalinadhabhotla | G01P 21/00 701/31.4 |
| 2011/0112766 | A1* | 5/2011 | Haran | G01S 5/04 701/469 |
| 2012/0004804 | A1* | 1/2012 | Beams | G01S 5/0027 701/32.7 |
| 2012/0286991 | A1* | 11/2012 | Chen et al. | 342/357.23 |
| 2012/0330497 | A1* | 12/2012 | De Tommasi | G01C 25/005 701/33.1 |
| 2013/0034138 | A1* | 2/2013 | Lee | H04R 3/005 375/224 |
| 2013/0060522 | A1* | 3/2013 | Dirndorfer | G08G 1/16 702/182 |

OTHER PUBLICATIONS

Douša, Jan, "Processing of Ground-Based GNSS Data to Produce Near Real-Time (NRT) Tropospheric zenith Path Delays (ZTD)," *EUMETNET GPS Water Vapour Programme (E-GVAP) Workshop*, Nov. 6, 2008, 32 pages, Copenhagen, retrieved from <http://egvap.dmi.dk/workshop/2-processing-of-GNSS-data-Dousa.pdf> on Jun. 17, 2013.

Author Unknown, "Global Navigation Satellite System (GNSS)," May 9, 2010, 39 pages, retrieved from <http://www.princeton.edu/~alaink/Orf467F07/GNSS.pdf> on Jun. 17, 2013.

Perry, John, et al., "Timing on the Fly, Synchronization for Direct Georeferencing on Small UAVs," *Inside GNSS*, Nov./Dec. 2009, pp. 34-40, retrieved from <http://www.insidegnss.com/node/1715> on Jun. 17, 2013.

Kumar, Arun, "GNSS Principles Tutorial: Determining the Accuracy of a GPS Device," *Bright Hub*, Jul. 19, 2009, 3 pages retrieved from <http://www.brighthub.com/electronics/gps/articles/42314.aspx> on Jun. 17, 2013.

European Space Agency (ESA), "Software Facilities," Jul. 12, 2004, 3 pages, retrieved from <http://www.esa.int/Our_Activities/Navigation/Software_facilities> on Jun. 17, 2013.

Mediatech-dif.com, "Related Search Results for GPS," <http://www.mediatec-dif.com/issfd/OrbidIII/Inoue.pdf> retrieved on Jun. 17, 2013, 2 pages.

Roberts, G.W., "Integrating Localities and GNSS for Engineering Works," *Proceedings of the 7th FIG Regional Conference, Spatial Data Servicing People: Land Governance and the Environment—Building Capacity*, Oct. 19-22, 2009, pp. 1-13, Vietnam, retrieved from <http://www.fig.net/pub/vietnam/papers/ts06d/ts06d_roberts_etal_3589.pdf> on Jun. 17, 2013.

Positim, "High Accuracy GNSS Solutions and Services," Sep. 2009, 3 pages, retrieved from <http://www.positim.com/index_gnss.html> on Jun. 17, 2013.

Santerre, Ph.D, Rock, "Book Review for Geomatica: GNSS Applications and Methods," Mar. 11, 2011, 2 pages, retrieved from <http://ebookbrowse.com/bookreviewgeomatica-0110-santerre-en-pdf-d78217493> on Jun. 17, 2013.

Sterzbach, Bernard, "GPS-Based Clock Synchronization in a Mobile, Distributed Real-Time System," *Real-Time Systems*, Jan. 1, 1997, pp. 63-75, vol. 12, retrieved from <http://www.springerlink.com/content/j5x05g85184j2376/> on Jun. 17, 2013.

Mach, Johannes, et al., "Real-Time Station Clock Synchronization for GNSS Integrity Monitoring," *Proceedings of the Institute of Navigation GNSS Meeting*, Sep. 13-16, 2005, 10 pages, California, retrieved from <http://www.ifen.com/content/publications/2005/ION2005_Synchronization_Paper.pdf> on Jun. 17, 2013.

GPS World, <http://www.gpsworld.com/gnss-system/integration-with-other-technologies/ion-gnss-keynote-the-big-three-issues-gpts-sustainme> accessed on Jun. 17, 2013.

Gleason, Scott, et al., "GNSS Applications and Methods," (Textbook), 2009, 530 pages, Artech House, USA.

* cited by examiner

DATA SYNCHRONIZATION ACROSS MULTIPLE SENSORS

TECHNOLOGICAL FIELD

Embodiments of the present invention relate generally to communication technology and, more particularly, relate to methods, systems, apparatus, and computer program products for performing data synchronization across multiple sensors.

BACKGROUND

A growing need exists in the fleet telematics and auto insurance industries to monitor driver behavior and vehicle parametric data in real time. Current telematics systems are increasingly relying on multiple sensors to provide real time data. This data is recorded and analyzed to better understand driver behavior, vehicle performance in different environmental conditions, and vehicle maintenance needs. All of this information allows users to assign insurance risk more accurately. The collected data is often used during post accident analysis to determine driver behavior and vehicle performance immediately prior to the accident. To provide the highest level of usefulness, the collected data used in the analysis from all sensors must be correctly time tagged and synchronized with each other.

Since providing reliable and highly accurate time can be expensive to implement, many telematics systems rely on the universal clock time provided by global positioning system (GPS) satellites. The data received from global navigation satellite system (GNSS) sensors typically contain a time stamp from a GPS satellite for when the data was measured. Various types of unpredictable delays may occur, however, prior to a telematics system receiving and/or recording GNSS sensor data. As a result, the universal time stamp contained in the data may not accurately correspond to the time the data is recorded by the telematics system. Therefore, associating the time the data is recorded with the time referenced in the universal time stamp may result in potentially significant errors due to the delay, particularly when comparing the GNSS sensor data to data from other sensors without universal time stamps.

Therefore, a need exists for synchronizing data across multiple sensors and tagging all sensor data with a common, reliable, universal time.

SUMMARY

In general, embodiments of the present invention provide methods, systems, apparatus, and computer program products for synchronizing data across at least two sensors.

In one aspect, a method for synchronizing data is provided. In one embodiment, the method comprises (1) recording first sensor data provided by at least one first sensor, wherein the first sensor data comprises a universal time stamp based on a universal time source; (2) recording second sensor data provided by at least one second sensor, wherein the second sensor data does not comprise a universal time stamp based on a universal time source; (3) correlating the first sensor data with the second sensor data; and (4) determining a universal time that corresponds to the at least one second sensor data based at least in part on the correlation between the first sensor data and the second sensor data.

According to another aspect, an apparatus comprising at least one processor and at least one memory including computer program code is provided. The at least one memory and the computer program code may be configured to, with the processor, cause the apparatus to at least (1) record first sensor data provided by at least one first sensor, wherein the first sensor data comprises a universal time stamp based on a universal time source; (2) record second sensor data provided by at least one second sensor, wherein the second sensor data does not comprise a universal time stamp based on a universal time source; (3) correlate the first sensor data with the second sensor data; and (4) determine a universal time that corresponds to the at least one second sensor data based at least in part on the correlation between the first sensor data and the second sensor data.

According to yet another aspect, a computer program product is provided. The computer program product may comprise at least one computer-readable storage medium having computer-readable program code portions stored therein, the computer-readable program code portions comprising executable portions configured to (1) record first sensor data provided by at least one first sensor, wherein the first sensor data comprises a universal time stamp based on a universal time source; (2) record second sensor data provided by at least one second sensor, wherein the second sensor data does not comprise a universal time stamp based on a universal time source; (3) correlate the first sensor data with the second sensor data; and (4) determine a universal time that corresponds to the at least one second sensor data based at least in part on the correlation between the first sensor data and the second sensor data.

BRIEF DESCRIPTION OF THE DRAWING(S)

Having thus described embodiments of the invention in general terms, reference will now be made to the accompanying drawings, which are not necessarily drawn to scale, and wherein:

DETAILED DESCRIPTION

Figure 1:
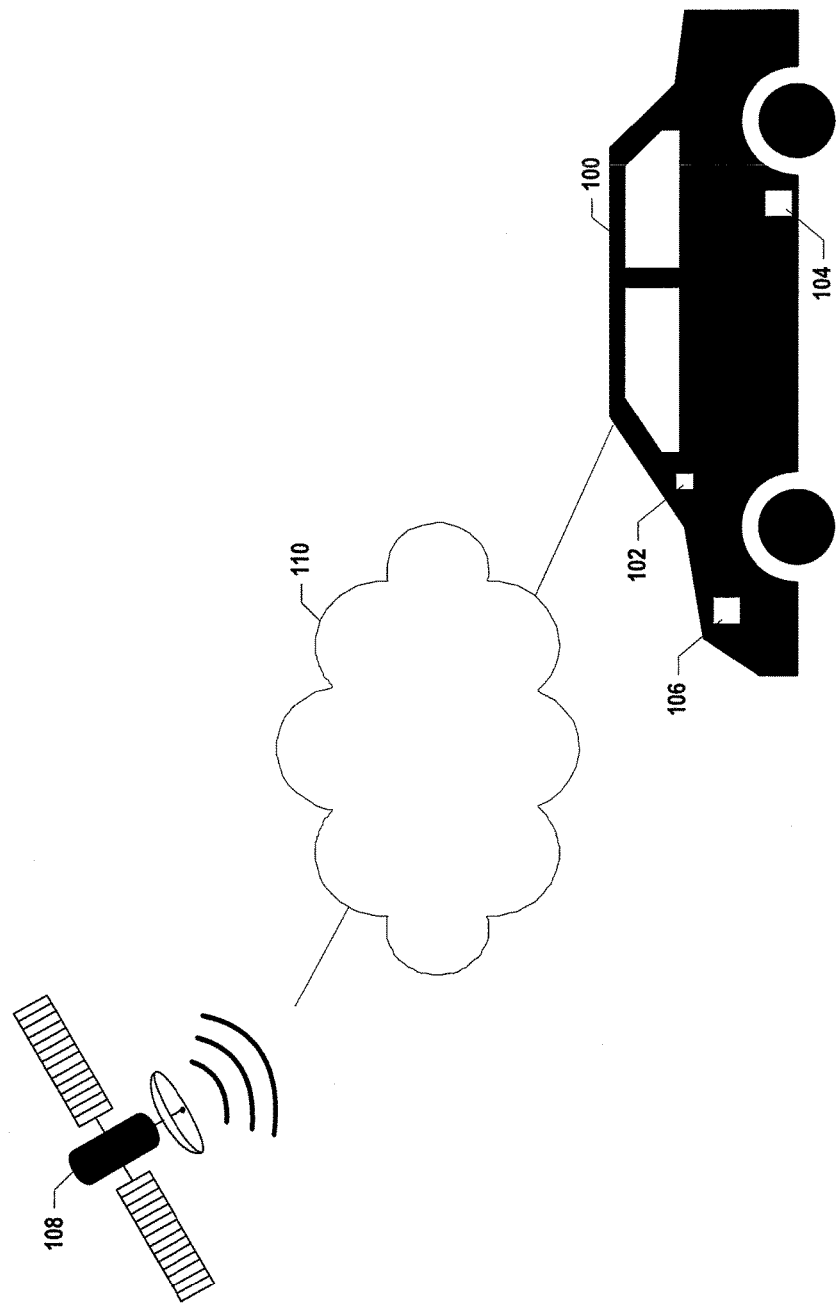
FIG. 1 illustrates a block diagram of one type of system that can be used to practice various embodiments of the present invention.

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein;

rather, these embodiments are provided so that this disclosure will satisfy applicable legal requirements. The term "or" is used herein in both the alternative and conjunctive sense, unless otherwise indicated. Like numbers refer to like elements throughout.

As should be appreciated, various embodiments may be implemented in various ways, including as methods, apparatus, systems, or computer program products. Accordingly, various embodiments may take the form of an entirely hardware embodiment or an embodiment in which a processor is programmed to perform certain steps. Furthermore, various implementations may take the form of a computer program product on a computer-readable storage medium having computer-readable program instructions embodied in the storage medium. Any suitable computer-readable storage medium may be utilized including hard disks, CD-ROMs, optical storage devices, or magnetic storage devices.

Various embodiments are described below with reference to block diagrams and flowchart illustrations of methods, apparatus, systems, and computer program products. It should be understood that each block of the block diagrams and flowchart illustrations, respectively, may be implemented in part by computer program instructions, e.g., as logical steps or operations executing on a processor in a computing system. These computer program instructions may be loaded onto a computer, such as a special purpose computer or other programmable data processing apparatus to produce a specifically-configured machine, such that the instructions which execute on the computer or other programmable data processing apparatus implement the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the functionality specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide operations for implementing the functions specified in the flowchart block or blocks.

Accordingly, blocks of the block diagrams and flowchart illustrations support various combinations for performing the specified functions, combinations of operations for performing the specified functions and program instructions for performing the specified functions. It should also be understood that each block of the block diagrams and flowchart illustrations, and combinations of blocks in the block diagrams and flowchart illustrations, can be implemented by special purpose hardware-based computer systems that perform the specified functions or operations, or combinations of special purpose hardware and computer instructions.

FIG. 1 provides an illustration of a system that can be used in conjunction with various embodiments of the present invention. As shown in FIG. 1, the system may include one or more vehicles 100, one or more terminal apparatuses 102, one or more vehicle sensors 104, one or more Global Navigation Satellite System (GNSS) sensors 106, one or more Global Positioning System (GPS) satellites 108, and one or more networks 110. Each of the components of the system may be in electronic communication with, for example, one another over the same or different wireless or wired networks including, for example, a wired or wireless Personal Area Network (PAN), Local Area Network (LAN), Metropolitan Area Network (MAN), Wide Area Network (WAN), or the like. Additionally, while FIG. 1 illustrates certain system entities as separate, standalone entities, the various embodiments are not limited to this particular architecture.

Figure 2:
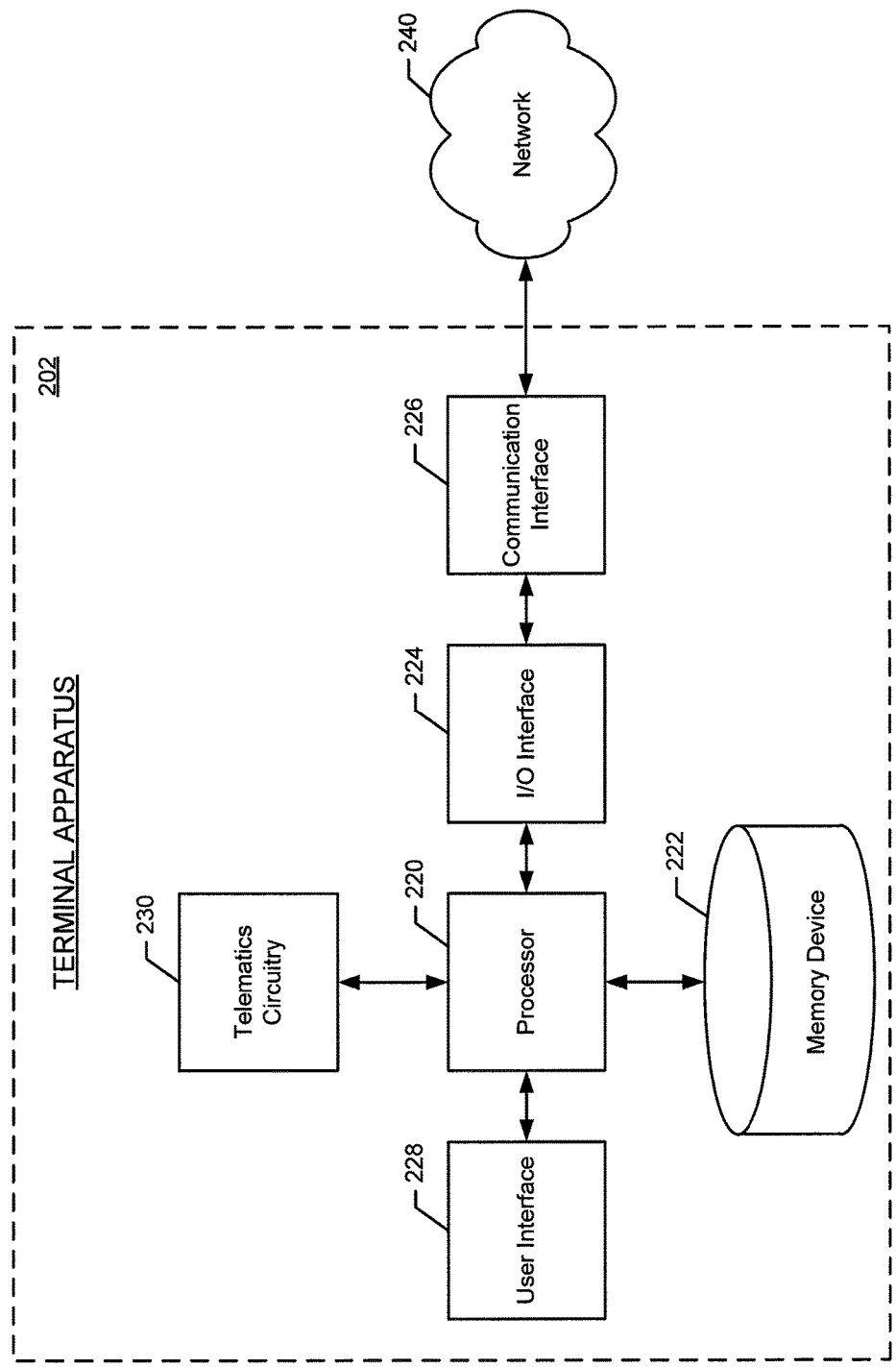
FIG. 2 illustrates a block diagram of a terminal apparatus that can be used to practice various embodiments of the present invention.

FIG. 2 illustrates a terminal apparatus 202 for synchronizing data across multiple sensors according to an example embodiment of the present invention. It will be appreciated that the scope of the invention encompasses many potential embodiments in addition to those illustrated and described herein. As such, while FIG. 2 illustrates one example of a configuration of a terminal apparatus 202 for synchronizing data across multiple sensors, numerous other configurations may also be used to implement embodiments of the present invention.

The terminal apparatus 202 may be embodied as a desktop computer, laptop computer, mobile terminal, mobile computer, mobile phone, mobile communication device, game device, digital camera/camcorder, audio/video player, television device, radio receiver, digital video recorder, sensor device, navigation device, positioning device, telematics device, server, network node, multiple computing devices in communication with each other, any combination thereof, and/or the like. In an example embodiment, the terminal apparatus 202 may be embodied as a telematics device 10, such as that illustrated in FIG. 3.

Figure 3:
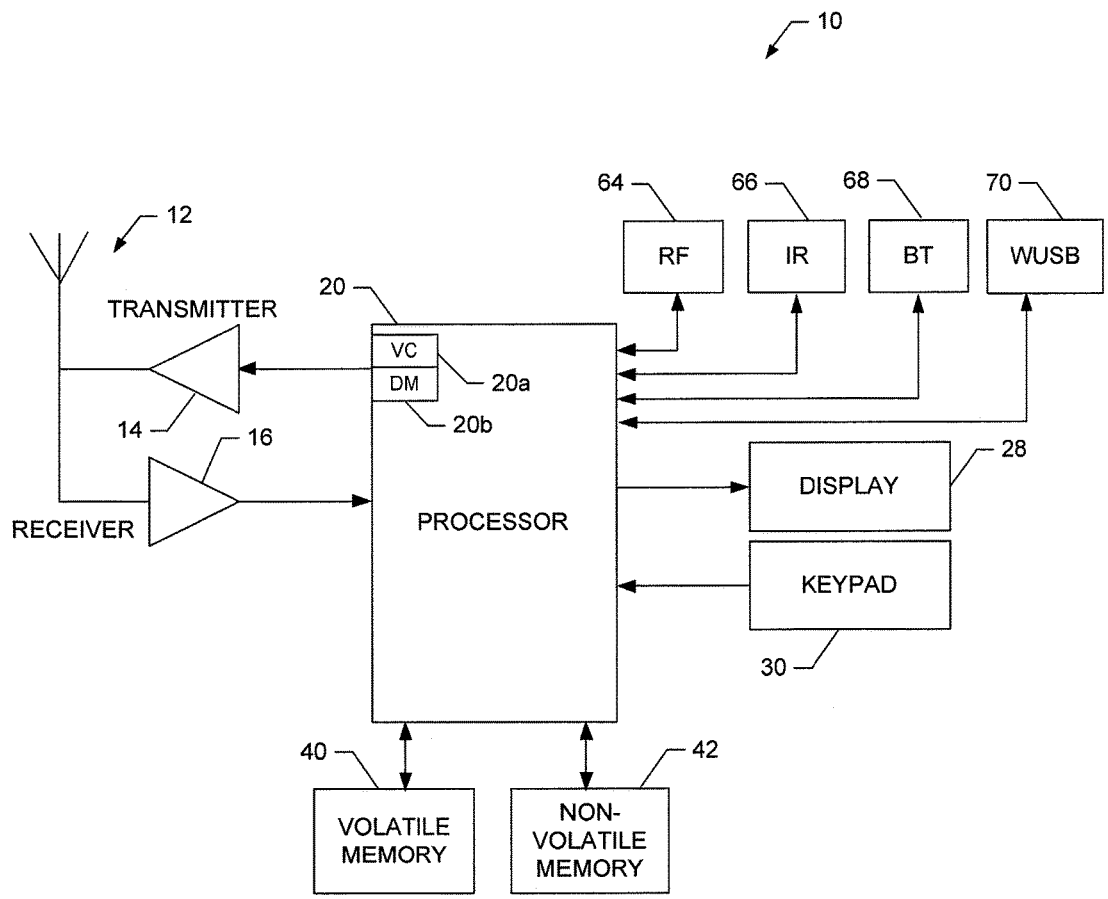
FIG. 3 illustrates a schematic block diagram of a terminal apparatus that can be used to practice various embodiments of the present invention.

In this regard, FIG. 3 illustrates a block diagram of a telematics device 10 representative of one embodiment of a terminal apparatus 202 in accordance with embodiments of the present invention. It should be understood, however, that the telematics device 10 illustrated and hereinafter described is merely illustrative of one type of terminal apparatus 202 that may implement and/or benefit from embodiments of the present invention and, therefore, should not be taken to limit the scope of the present invention. While several embodiments of the electronic device are illustrated and will be hereinafter described for purposes of example, other types of electronic devices, such as mobile telephones, mobile computers, portable digital assistants (PDAs), pagers, laptop computers, desktop computers, gaming devices, televisions, navigation systems, and any other type of electronic system, may employ embodiments of the present invention.

As shown, the telematics device 10 may include an antenna 12 (or multiple antennas 12) in communication with a transmitter 14 and a receiver 16. The telematics device 10 may also include a processor 20 that provides signals to and receives signals from the transmitter and receiver, respectively. These signals may include signaling information in accordance with an air interface standard of an applicable cellular system, and/or any number of different wireline or wireless networking techniques, comprising but not limited to Wi-Fi™, wireless local access network (WLAN) techniques such as Institute of Electrical and Electronics Engineers (IEEE) 802.11, 802.16, and/or the like. In addition, these signals may include speech data, user generated data, user requested data, and/or the like. In this regard, the telematics device 10 may be capable of operating with one or more air interface standards, communication protocols, modulation types, access types, and/or the like. More particularly, the telematics device 10 may be capable of operating in accordance with various first generation (1G), second generation (2G), 2.5G, third-generation (3G) communication protocols, fourth-generation (4G) communication protocols, Internet Protocol Multimedia Subsystem (IMS) communication protocols (e.g., session initiation protocol (SIP)), and/or the like. For example, the telematics device 10 may be capable of operating in accordance with 2G wireless communication protocols IS-136 (Time Division Multiple Access (TDMA)), Global System for Mobile communications (GSM), IS-95 (Code Division Multiple Access (CDMA)), and/or the like. Also, for example, the telematics device 10 may be capable of operating in accordance with 2.5G wireless communication protocols General Packet Radio Service (GPRS), Enhanced Data GSM Environment (EDGE), and/or the like. Further, for example, the telematics device 10 may be capable of operating in accordance with 3G wireless communication protocols such as Universal Mobile Telecommunications System (UMTS), Code Division Multiple Access 2000 (CDMA2000), Wideband Code Division Multiple Access (WCDMA), Time Division-Synchronous Code Division Multiple Access (TD-SCDMA), and/or the like. The telematics device 10 may be additionally capable of operating in accordance with 3.9G wireless communication protocols such as Long Term Evolution (LTE) or Evolved Universal Terrestrial Radio Access Network (E-UTRAN) and/or the like. Additionally, for example, the telematics device 10 may be capable of operating in accordance with fourth-generation (4G) wireless communication protocols and/or the like as well as similar wireless communication protocols that may be developed in the future. Additionally, the telematics device 10 may be capable of operating according to Wireless Fidelity (Wi-Fi) or Worldwide Interoperability for Microwave Access (Wi-MAX) protocols.

It is understood that the processor 20 may comprise circuitry for implementing audio/video and logic functions of the telematics device 10. For example, the processor 20 may be embodied as various means including circuitry, one or more microprocessors with accompanying digital signal processor(s), one or more processor(s) without an accompanying digital signal processor, one or more coprocessors, one or more multi-core processors, one or more controllers, processing circuitry, one or more computers, various other processing elements including integrated circuits, such as, for example, an ASIC (application specific integrated circuit) or FPGA (field programmable gate array), or some combination thereof. The processor may additionally comprise an internal voice coder (VC) 20a, an internal data modem (DM) 20b, and/or the like. Further, the processor may comprise functionality to operate one or more software programs, which may be stored in memory. For example, the processor 20 may be capable of operating a connectivity program, such as a web browser. The connectivity program may allow the telematics device 10 to transmit and receive web content, such as location-based content, according to a protocol, such as Wireless Application Protocol (WAP), hypertext transfer protocol (HTTP), and/or the like. The telematics device 10 may be capable of using a Transmission Control Protocol/Internet Protocol (TCP/IP) to transmit and receive web content across the internet or other networks.

The telematics device 10 may also comprise a user interface including, for example, a display 28, a user input interface, and/or the like, which may be operationally coupled to the processor 20. In this regard, the processor 20 may comprise user interface circuitry configured to control at least some functions of one or elements of the user interface, such as, for example, the display 28 and/or the like. The processor 20 and/or user interface circuitry comprising the processor 20 may be configured to control one or more functions of one or more elements of the user interface through computer program instructions (e.g., software and/or firmware) stored on a memory accessible to the processor 20 (e.g., volatile memory 40, non-volatile memory 42, and/or the like). The telematics device 10 may comprise a battery for powering various circuits related to the telematics device 10, for example, a circuit to provide mechanical vibration as a detectable output. The user input interface may comprise devices allowing the telematics device 10 to receive data, such as a keypad 30, a touch display, a joystick, and/or other input device. In embodiments including a keypad, the keypad may comprise numeric (0-9) and related keys (#, *), and/or other keys for operating the telematics device 10.

As shown in FIG. 3, the telematics device 10 may also include one or more means for sharing and/or obtaining data. For example, the telematics device 10 may comprise a short-range radio frequency (RF) transceiver and/or interrogator 64 so data may be shared with and/or obtained from electronic devices in accordance with RF techniques. The telematics device 10 may comprise other short-range transceivers, such as, for example, an infrared (IR) transceiver 66, a Bluetooth™ (BT) transceiver 68 operating using Bluetooth™ brand wireless technology developed by the Bluetooth™ Special Interest Group, a wireless universal serial bus (USB) transceiver 70 and/or the like. The Bluetooth™ transceiver 68 may be capable of operating according to ultra-low power Bluetooth™ technology (e.g., Wibree™) radio standards. In this regard, the telematics device 10 and, in particular, the short-range transceiver may be capable of transmitting data to and/or receiving data from electronic devices within a proximity of the telematics device 10, such as within 10 meters, for example. The telematics device 10 may be capable of transmitting and/or receiving data from electronic devices according to various wireless networking techniques, including Wireless Fidelity (Wi-Fi), WLAN techniques such as IEEE 802.11 techniques, IEEE 802.11u techniques, IEEE 802.16 techniques, Wi-Fi Alliance (WFA) techniques, and/or the like.

The telematics device 10 may comprise other removable and/or fixed memory. The telematics device 10 may include volatile memory 40 and/or non-volatile memory 42. For example, volatile memory 40 may include Random Access Memory (RAM) including dynamic and/or static RAM, on-chip or off-chip cache memory, and/or the like. Non-volatile memory 42, which may be embedded and/or removable, may include, for example, read-only memory, flash memory, magnetic storage devices (e.g., hard disks, floppy disk drives, magnetic tape, etc.), optical disc drives and/or media, non-volatile random access memory (NVRAM), and/or the like. Like volatile memory 40 non-volatile memory 42 may include a cache area for temporary storage of data. The memories may store one or more software programs, instructions, pieces of information, data, and/or the like which may be used by the telematics device 10 for performing functions of the telematics device 10.

Returning now to FIG. 2, in an example embodiment the terminal apparatus 202 includes various means, such as a processor 220, memory 222, I/O interface 224, communication interface 226, user interface 228, and telematics circuitry 230 for performing the various functions herein described. These means of the terminal apparatus 202 as described herein may be embodied as, for example, circuitry, hardware elements (e.g., a suitably programmed processor, combinational logic circuit, and/or the like), a computer program product comprising computer-readable program instructions (e.g., software or firmware) stored on a computer-readable medium (e.g. memory 222) that is executable by a suitably configured processing device (e.g., the processor 220), or some combination thereof.

The processor 220 may, for example, be embodied as various means including one or more microprocessors with accompanying digital signal processor(s), one or more processor(s) without an accompanying digital signal processor, one or more coprocessors, one or more multi-core processors, one or more controllers, processing circuitry, one or more computers, various other processing elements including integrated circuits such as, for example, an ASIC (application specific integrated circuit) or FPGA (field programmable gate array), or some combination thereof. Accordingly, although illustrated in FIG. 2 as a single processor, in some embodiments the processor 220 comprises a plurality of processors. The plurality of processors may be embodied on a single computing device or may be distributed across a plurality of computing devices collectively configured to function as the terminal apparatus 202. The plurality of processors may be in operative communication with each other and may be collectively configured to perform one or more functionalities of the terminal apparatus 202 as described herein. In embodiments wherein the terminal apparatus 202 may be embodied as a telematics device 10, the processor 220 may be embodied as or comprise the processor 20. In an example embodiment, the processor 220 may be configured to execute instructions stored in the memory 222 or otherwise accessible to the processor 220. These instructions, when executed by the processor 220, may cause the terminal apparatus 202 to perform one or more of the functionalities of the terminal apparatus 202 as described herein. As such, whether configured by hardware or software methods, or by a combination thereof, the processor 220 may comprise an entity capable of performing operations according to embodiments of the present invention while configured accordingly. Thus, for example, when the processor 220 is embodied as an ASIC, FPGA or the like, the processor 220 may comprise specifically configured hardware for conducting one or more operations described herein. Alternatively, as another example, when the processor 220 is embodied as an executor of instructions, such as may be stored in the memory 222, the instructions may specifically configure the processor 220 to perform one or more algorithms and operations described herein.

The memory 222 may include, for example, volatile and/or non-volatile memory. Although illustrated in FIG. 2 as a single memory, the memory 222 may comprise a plurality of memories. The plurality of memories may be embodied on a single computing device or distributed across a plurality of computing devices. The memory 222 may comprise volatile memory, non-volatile memory, or some combination thereof. In this regard, the memory 222 may comprise, for example, a hard disk, random access memory, cache memory, flash memory, a compact disc read only memory (CD-ROM), digital versatile disc read only memory (DVD-ROM), an optical disc, circuitry configured to store information, or some combination thereof. In embodiments wherein the terminal apparatus 202 is embodied as a telematics device 10, the memory 222 may comprise the volatile memory 40 and/or the non-volatile memory 42. The memory 222 may be configured to store information, data, applications, instructions, or the like for enabling the terminal apparatus 202 to carry out various functions in accordance with embodiments of the present invention. For example, in at least some example embodiments, the memory 222 may be configured to buffer input data for processing by the processor 220. Additionally or alternatively, in at least some example embodiments, the memory 222 may be configured to store program instructions for execution by the processor 220. The memory 222 may store information in the form of static and/or dynamic information. This stored information may be stored and/or used by the telematics circuitry 230 during the course of performing their functionalities.

The I/O interface 224 may be any device, circuitry, or means embodied in hardware, a computer program product, or a combination of hardware and a computer program product that is configured to interface the processor 220 with other circuitry or devices, such as the communication interface 226. In some example embodiments, the I/O interface 224 may embody or be in communication with a bus that is shared by multiple components. In some example embodiments, the processor 220 may interface with the memory 222 via the I/O interface 224. The I/O interface 224 may be configured to convert signals and data into a form that may be interpreted by the processor 220. The I/O interface 224 may also perform buffering of inputs and outputs to support the operation of the processor 220. According to some example embodiments, the processor 220 and the I/O interface 224 may be combined onto a single chip or integrated circuit configured to perform, or cause the terminal apparatus 202 to perform, various functionalities of the present invention.

In some embodiments, the terminal apparatus 202 or some of the components of terminal apparatus 202 (e.g., the processor 220 and the memory 222) may be embodied as a chip or chip set. In other words, the terminal apparatus 202 may comprise one or more physical packages (e.g., chips) including materials, components and/or wires on a structural assembly (e.g., a baseboard). The structural assembly may provide physical strength, conservation of size, and/or limitation of electrical interaction for component circuitry included thereon. The terminal apparatus 202 may therefore, in some cases, be configured to implement embodiments of the present invention on a single chip or as a single "system on a chip." As such, in some cases, a chip or chipset may constitute means for performing the functionalities described herein and with respect to the processor 220.

The communication interface 226 may be embodied as any device or means embodied in circuitry, hardware, a computer program product comprising computer readable program instructions stored on a computer readable medium (e.g., the memory 222) and executed by a processing device (e.g., the processor 220), or a combination thereof that is configured to receive and/or transmit data from/to a network 240 and/or any other device, such as, for example, a third party entity (e.g. the one or more GPS satellites 106 illustrated in FIG. 1) and/or the like. In at least one embodiment, the communication interface 226 may be at least partially embodied as or otherwise controlled by the processor 220. In this regard, the communication interface 226 may be in communication with the processor 220, such as via a bus. The communication interface 226 may include, for example, an antenna, a transmitter, a receiver, a transceiver and/or supporting hardware or software for enabling communications with another computing device. The communication interface 226 may be configured to receive and/or transmit data using any protocol that may be used for communications between computing devices. The communication interface 226 may additionally be in communication with the memory 222, I/O interface 224, user interface 228, and/or telematics circuitry 230, such as via a bus.

The user interface 228 may be in communication with the processor 220 to receive an indication of a user input and/or to provide an audible, visual, mechanical, or other output to a user. As such, the user interface 228 may include, for example, a keyboard, a mouse, a joystick, a display, a touch screen display, a microphone, a speaker, and/or other input/output mechanisms. In embodiments wherein the terminal apparatus 202 is embodied as a server, aspects of the user interface 228 may be reduced or the user interface 228 may even be eliminated. Alternatively, in embodiments wherein the terminal apparatus 202 is embodied as a server, at least some aspects of the user interface 228 may be embodied on an apparatus used by a user that is in communication with the terminal apparatus 202. The user interface 228 may be in communication with the memory 222, I/O interface 224, communication interface 226, and/or telematics circuitry 230, such as via a bus.

The telematics circuitry 230 may be embodied as various means, such as circuitry, hardware, a computer program product comprising computer readable program instructions stored on a computer readable medium (e.g., the memory 222) and executed by a processing device (e.g., the processor 220), or some combination thereof and, in one embodiment, may be embodied as or otherwise controlled by the processor 220. In embodiments wherein the telematics circuitry 230 is embodied separately from the processor 220, the telematics circuitry 230 may be in communication with the processor 220. According to various embodiments, the telematics circuitry 230 may be in further communication with the one or more vehicle sensors 104 and/or one or more Global Navigation Satellite System (GNSS) sensors 106, as shown in FIG. 1. In some embodiments, the telematics circuitry 230 may comprise the one or more vehicle sensors 104 and/or one or more Global Navigation Satellite System (GNSS) sensors 106. The telematics circuitry 230 may further be in communication with one or more of the memory 222, I/O interface 224, communication interface 226, or user interface 228, such as via a bus. The telematics circuitry 230 may be configured to synchronize data across multiple sensors. According to example embodiments, the telematics circuitry 230 may also be configured to assign a universal time stamp to sensor data without a universal time stamp.

Figure 4:
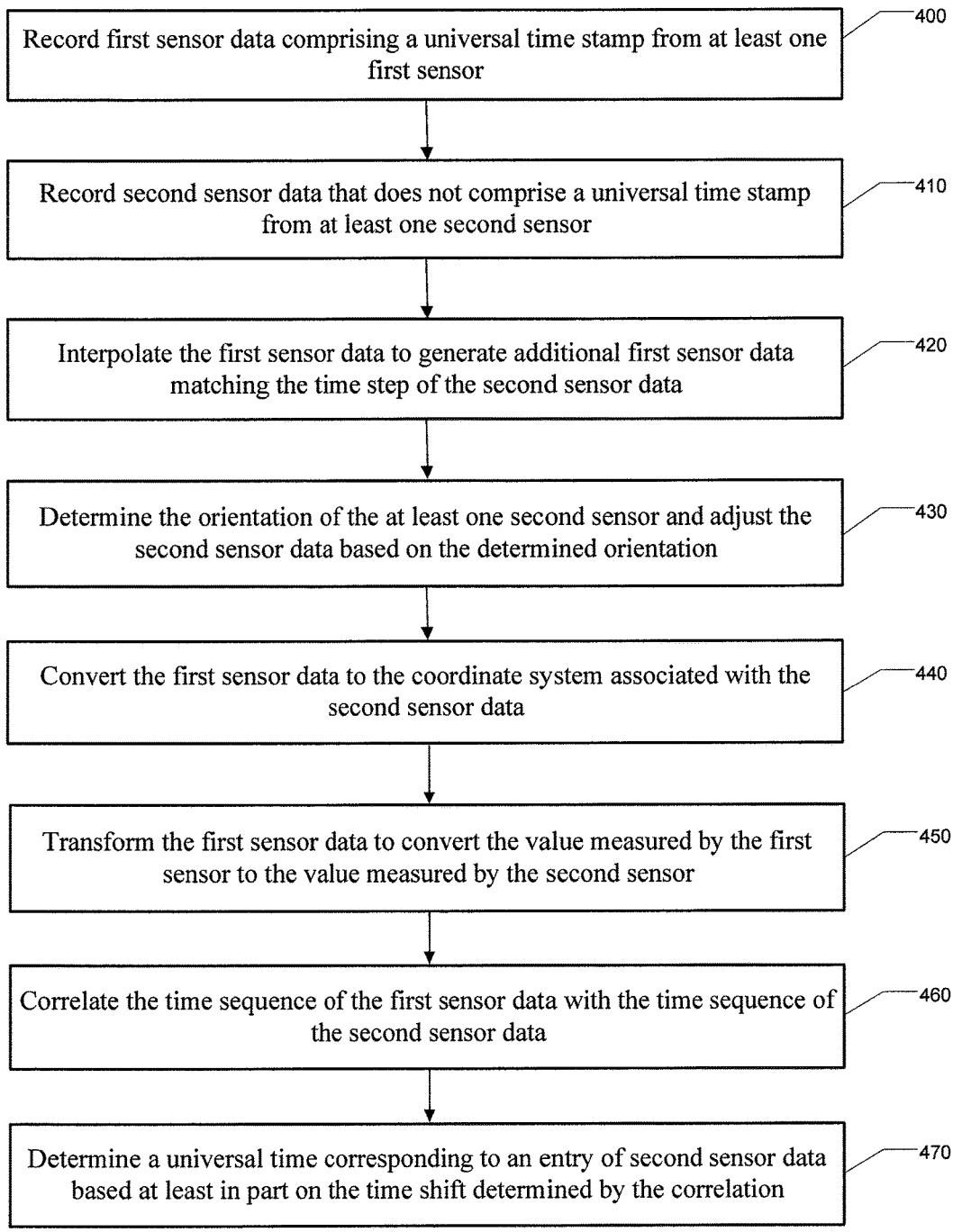
FIG. 4 illustrates a flowchart including operations and processes that can be used in accordance with various embodiments of the present invention.

Reference will now be made to FIG. 4. FIG. 4 illustrates a flowchart according to an example method for synchronizing data across multiple sensors according to an example embodiment of the invention. In this regard, FIG. 4 illustrates operations and processes that may be performed by the telematics circuitry 230.

In one embodiment, as shown in FIG. 4, the process may begin at operation 400 when a telematics device may record data from at least one first sensor. The data from the first sensor may be marked with a time stamp corresponding to the time the data was measured. For example, in various embodiments, the first sensor may be a Global Navigation Satellite System (GNSS) sensor, and the data may be time stamped using a reliable and highly accurate absolute universal time clock, such as Coordinated Universal Time (UTC). In these embodiments, the GNSS sensor may maintain UTC by synchronizing with one or more Global Positioning System (GPS) satellites, as is known in the art. The GNSS sensor may, therefore, know UTC to within an accuracy of tens of nanoseconds.

In certain embodiments, when the telematics device records data from the first sensor, the telematics device may further associate the data with a local time stamp, such as from the internal clock of the processor, corresponding to the time the data is recorded by the telematics device. According to certain embodiments, the local time stamp may be based on an incrementing counter in the processor that begins at an arbitrary zero moment. Alternatively, the local time stamp may be based on a local clock time of the telematics device that may or may not be synchronized with an absolute universal time clock. In these embodiments, therefore, the data from the first sensor may have both an absolute universal clock time stamp corresponding to the time at which the data was measured and a local time stamp corresponding to the time at which the data was recorded by the telematics device.

The time at which the first sensor data is measured may differ significantly from the time at which the first sensor data is recorded for various reasons. In some embodiments, the GNSS sensor may provide more data than a universal clock time. For example, the GNSS sensor may additionally provide position, velocity, and time (PVT) values such as time, latitude, longitude, altitude, and/or velocity. These values may require computation prior to the GNSS sensor outputting the data. According to some embodiments, these computations may occur at a low priority compared to the time synchronization and other operations. As a result, a delay may occur between the time at which the data is measured and stamped with the universal time and the time at which the PVT values have been computed and output from the GNSS sensor. Such a delay may be from half a second to a full second or greater.

According to various embodiments, a further delay may be incurred during the transmission of the data from the GNSS sensor to the telematics device. In some embodiments, data may be transmitted from the GNSS sensor to the telematics device via National Marine Electronics Association (NMEA) messages, and/or the like. These NMEA messages may comprise ASCII strings. According to example embodiments, the NMEA messages may be transmitted over a serial, asynchronous wired connection. As a result, delays may occur due to the time for propagating the messages over the serial connection. Additionally, in some embodiments, the scheduling software for serial port communication may assign a low priority to these messages, which can result in further delay when higher priority tasks are simultaneously using the serial port connection. Such a delay may be an additional 100 to 150 milliseconds or more. In alternative embodiments, similar delays may result from priority, scheduling, and/or propagation time related to transmission of the data from the GNSS sensor to the telematics device when different forms of wired and/or wireless communication are used. According to certain embodiments, the GNSS sensor may be embodied as a part of the telematics device, however, delays may still result within the telematics device during transmission of the data from the sensor to the recording circuitry of the telematics device.

In some embodiments, a further delay may result due to buffering of the received data by the telematics device. For example, in embodiments that rely on serial port communication between the GNSS sensor and the telematics device, the data may be initially stored in a serial port queue buffer before being recorded by the telematics device. This delay may occur even when the serial communication port is ready. In certain embodiments, this buffering may add an additional delay of tens of milliseconds or more.

In example embodiments, the discrepancy between the local time stamp and the universal time stamp due to the above mentioned delays may be resolved by the telematics device. At operation 410, the telematics device may record additional data from at least one second sensor. For example, in various embodiments, the second sensor may be a sensor for measuring acceleration, such as an accelerometer sensor. The data from the second sensor may not have a time stamp from a universal time source corresponding to the time at which the data was measured. In certain embodiments, when the telematics device records data from the second sensor, the telematics device may associate the data with a local time stamp, such as from the internal clock of the processor, corresponding to the time the data is recorded by the telematics device. In these embodiments, therefore, both the first sensor data and the second sensor data will each be marked with a local time stamp based on a time from the same local source.

In certain embodiments, the GNSS sensor and the accelerometer sensor may be configured to provide sensor data related to the same subject. According to an example embodiment, the GNSS sensor and accelerometer sensor may both be mounted to the same vehicle, and the data provided from each sensor may relate to the vehicle. The GNSS sensor data and the accelerometer sensor data may measure similar information but at different sampling rates and at different times. In some embodiments, although both the GNSS sensor data and the accelerometer sensor data may be associated with a local time stamp based on the time each was recorded by the telematics device, the local time stamps may not correspond to the actual measurement times of the data, due at least in part to the delays previously described. Accordingly, the data recorded from the GNSS sensor and the accelerometer sensor having the same local time stamp may relate to measurements taken at different times. In various embodiments, the difference between the local time stamps and the actual measurement times of the GNSS and accelerometer sensor data may be determined by the telematics device using the data from both the GNSS sensor and the accelerometer sensor.

According to various embodiments, at operation 420, the time step, that is, the time between data points (whether measured or interpolated data points), of the first sensor data may be adjusted to match the time step of the second sensor data. Alternatively, the time step of the second sensor data may be adjusted to match the time step of the first sensor data if the time step of the first sensor data is shorter than the time step of the second sensor data. In certain embodiments, the sample rate of the GNSS sensor may be lower than the sample rate of the accelerometer sensor. For example, the sample rate of the GNSS sensor may be around one hertz (Hz), or one sample per second. The accelerometer sensor may be polled at a rate at least as fast as the measurements are available, which may be about 20 to 50 times per second or a rate of about 20 to 50 Hertz. As a result, the maximum time delay of the accelerometer sensor may be less than the sensor integration time, or approximately 20 to 50 milliseconds.

In an example embodiment, to facilitate the comparison of the GNSS sensor data to the accelerometer sensor data, the time step of the GNSS sensor may be adjusted to the time step of the accelerometer sensor by interpolating GNSS sensor data points between the known GNSS sensor data points. According to various embodiments, spline interpolation may be used to determine the GNSS sensor data points at the same time step as the accelerometer sensor data. Alternative interpolation methods, such as linear interpolation, polynomial interpolation, and/or the like, may also be used to interpolate the GNSS sensor time step to match the accelerometer sensor time step.

Figure 5:
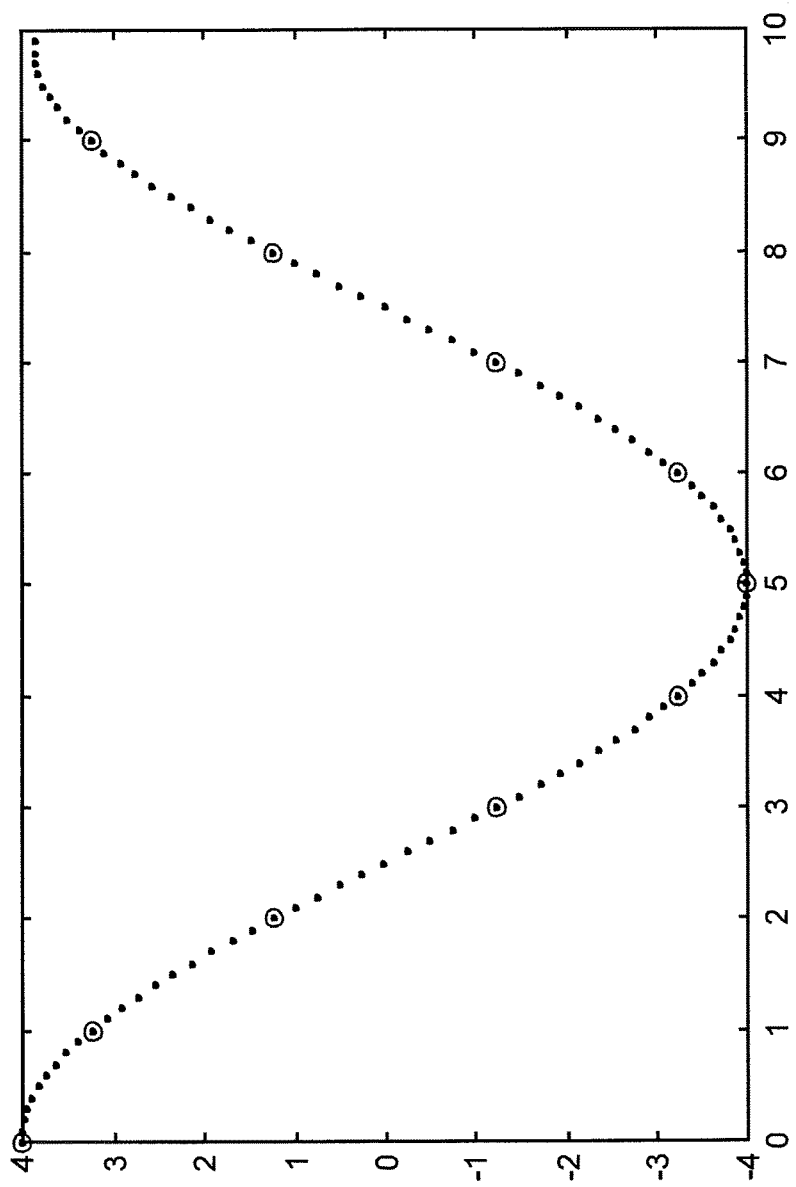
FIG. 5 illustrates an example curve generated using spline interpolation on a set of data points in accordance with various embodiments of the present invention.

FIG. 5 shows an example curve generated using spline interpolation on a set of data points, for example GNSS sensor data. In FIG. 5, the circled points may correspond to the actual data provided by the GNSS sensor to the telematics device. Spline interpolation may be used to provide additional data points between the actual data points, as represented by the non-circled dots. Accordingly, spline interpolation may be used to adjust the time step of the GNSS sensor data to the time step of a different set of sensor data sampled at a higher rate.

In various embodiments, the coordinate system of the first sensor data may be converted to the coordinate system of the second sensor data. According to example embodiments, the GNSS sensor data may be measured in an absolute Earth based coordinate system, such as the local East, North, Up (ENU) Cartesian coordinate system. The GNSS sensor data may also be measured in other Earth based coordinate systems such as Earth-centered, Earth-fixed (ECEF or ECF); local North, East, Down (NED); any Geodetic system; and/or the like. In these embodiments, the GNSS sensor data may be measured in a constant reference frame.

According to various embodiments, the accelerometer sensor data may be measured in a coordinate system using tangential and normal components. In these embodiments, the reference system of the accelerometer sensor may change as the position of the accelerometer sensor changes. For example, the accelerometer sensor may be mounted in a vehicle, and therefore, the reference frame of the accelerometer sensor may change as the position of the vehicle changes. In these embodiments, therefore, the accelerometer sensor data may not be measured in a constant reference frame.

Figure 6:
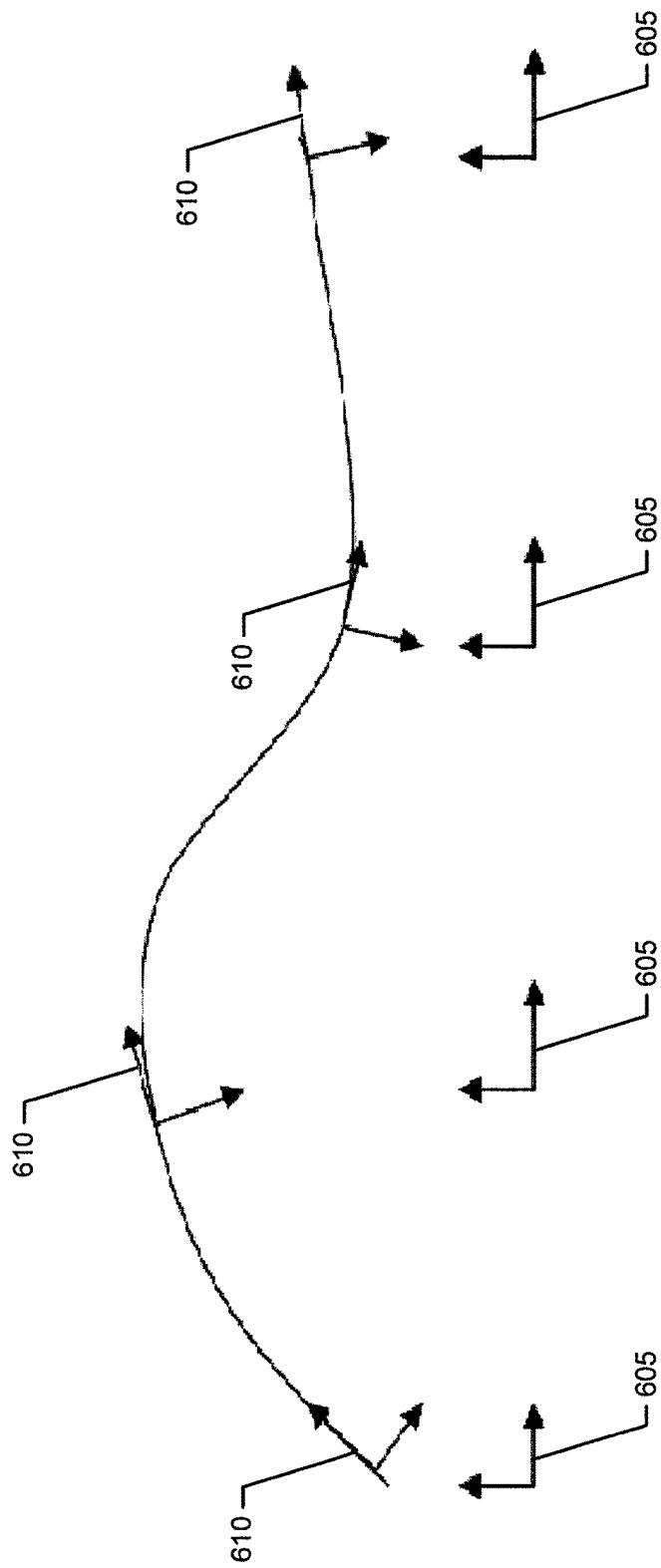
FIG. 6 illustrates an example trajectory measured by multiple sensors using different coordinate systems in accordance with various embodiments of the present invention.

FIG. 6 shows an example trajectory measured by multiple sensors. As shown in FIG. 6, data points represented by vectors 605, 610 may be measured in different coordinate systems by different sensors. For example, in one embodiment, a first sensor, such as a GNSS sensor, may measure data according to a constant reference frame coordinate system, such as the local ENU coordinate system, as depicted by vectors 605. A second sensor, such as an accelerometer sensor, may alternatively measure data according to vectors comprising tangential and normal components, such as vectors 610. FIG. 6 therefore provides an example of two sets of data representing values associated with a trajectory measured at the same time by different sensors in different coordinate systems.

According to embodiments where the accelerometer sensor is mounted, for example in a vehicle, the position of the accelerometer sensor as mounted may be determined to facilitate adjustment based on orientation. In certain embodiments, a major force measured by the accelerometer sensor may be gravity. Accordingly, if the accelerometer sensor is not mounted in a horizontal position, for example if the accelerometer is mounted at an incline or decline, the accelerometer sensor data may appear to suggest that the accelerometer is moving when it is not, due to the force of gravity. Similarly, if the vehicle containing the accelerometer sensor is positioned on an incline or a decline, gravity may have the same misleading effect on interpretation of the data.

In some embodiments, a correction may be made for the orientation of the accelerometer sensor based on the accelerometer sensor data at operation 430. The accelerometer sensor may move along a horizontal path to provide a trajectory segment of horizontal movement. For example, a segment of accelerometer sensor data may be analyzed for a vehicle to which the accelerometer sensor is mounted when the vehicle travels horizontally. Alternatively or additionally, according to certain embodiments, an adjustment for the orientation of the accelerometer sensor may be made based on the vertical acceleration component of the accelerometer sensor data.

In example embodiments, once the orientation of the accelerometer is known, the coordinate system of the GNSS sensor data may be converted to the coordinate system of the accelerometer sensor data at operation 440. According to alternative embodiments, the coordinate system of the accelerometer sensor data may be converted to the coordinate system of the GNSS sensor data.

According to various embodiments, the GNSS sensor may measure data related to the data measured by the accelerometer sensor. In an example embodiment, the GNSS sensor may measure the velocity of the vehicle to which it is mounted. The accelerometer sensor may measure the acceleration of the vehicle to which it is mounted. According to certain embodiments, the acceleration data and the velocity data may be measured in the same coordinate system. In alternative embodiments, the acceleration data and the velocity data may be measured in different coordinate systems, and the coordinate system of a first set of data may be converted to the same coordinate system of the second set of data, as described above with respect to operation 440.

In an example embodiment, at operation 450, the acceleration data of the accelerometer sensor may be transformed to velocity data. For example, the acceleration data may be integrated to convert the acceleration data to velocity data. The converted velocity data of the accelerometer sensor may be represented in the same coordinate system as the velocity data of the GNSS sensor. As a result of the conversion, in example embodiments, the telematics device may have two sets of corresponding velocity data in the same coordinate system for the same vehicle trajectory measured by two different sensors. According to alternative embodiments, the velocity data of the GNSS sensor may be transformed to acceleration data. For example, the velocity data may be differentiated to convert the velocity data to acceleration data.

At operation 460, according to various embodiments, correlation may be performed to determine the time shift between the velocity data set from the first sensor and the velocity data set from the second sensor. Various techniques may be used to perform the correlation, such as cross-correlation or the like. For example, in an embodiment using cross-correlation, each set of data may be considered as a function of time, namely the time from the internal clock of the processor used to generate the local time stamps. In example embodiments, the function of the GNSS sensor data set may be multiplied with the function of the accelerometer sensor data set. The function of the GNSS sensor data set may then be shifted by a unit of time and multiplied again by the function of the accelerometer sensor data set. This process may be continued until the product of the function of the GNSS sensor data set and the function of the accelerometer sensor data set is maximized. According to example embodiments, the point at which the product is maximized may indicate when the velocity data of the GNSS sensor is aligned in time with the velocity data of the accelerometer sensor. Therefore, the correlation may allow the telematics device to determine the time shift between the GNSS sensor data set and the accelerometer sensor data set. The time shift may be measured based on the units of the local time stamps of the GNSS and accelerometer sensor data sets, for example clock ticks of the internal clock of a processor. In an example embodiment, the telematics device may store the time shift.

Figure 7:
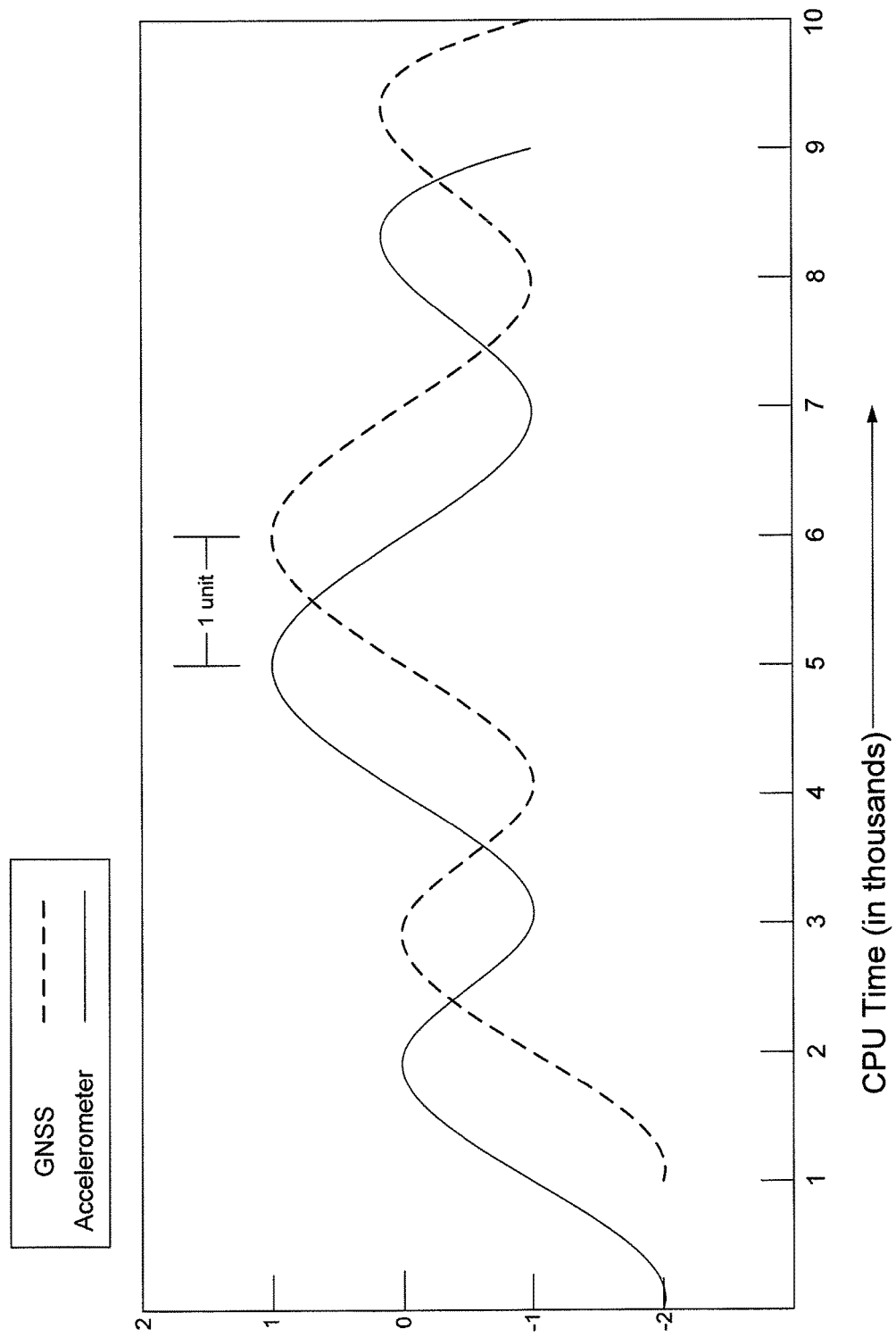
FIG. 7 illustrates an example of using correlation to determine a time shift between the time sequences of multiple sensors in accordance with various embodiments of the present invention.

FIG. 7 shows an example of using correlation to determine a time shift between GNSS sensor data and accelerometer sensor data. As shown in FIG. 7, the curve representing GNSS sensor data (i.e. the dotted line curve) may be delayed with respect to the accelerometer sensor data (i.e. the solid line curve). According to an example embodiment, the cross-correlation performed during operation 460, as described above, may determine that the time shift between the two curves is equal to one unit, or one thousand processor clock ticks, as shown in FIG. 7.

In various embodiments, the time shift may be used to calculate a universal time stamp for accelerometer sensor data at operation 470. For example, an entry of accelerometer sensor data may have a local time stamp but no universal time stamp. According to certain embodiments, the telematics device may reference an entry of GNSS sensor data having both a local time stamp and a universal time stamp. The entry of GNSS sensor data may correspond to the same event as the entry of accelerometer sensor data, or in certain embodiments an earlier event or a later event. The telematics device may then calculate the universal time of the entry of accelerometer sensor data using the local time stamp of the entry of accelerometer sensor data, the local time stamp of the entry of GNSS sensor data, the universal time of the entry of GNSS sensor data, and the time shift.

In an example embodiment, the telematics device may determine the amount of time that has elapsed between the occurrence of the event measured by the entry of GNSS sensor data and the occurrence of the event measured by the entry of accelerometer sensor data by subtracting the value in the local time stamp for the entry of GNSS sensor data from the value in the local time stamp for the entry of accelerometer sensor data and adding the time shift. In some embodiments, the elapsed time may then be converted from local time units to universal time units. For example, the elapsed time may be converted from processor clock ticks to hours, minutes, seconds, and parts of a second. According to various embodiments, the converted elapsed time may be added to the value of the universal time stamp of the entry of GNSS sensor data. The result of the calculation may provide the universal time corresponding to the event measured by the entry of accelerometer sensor data. The universal time may be accurate to within an error about equal to or less than the accelerometer sensor integration time. In certain embodiments, the telematics device may assign a universal time stamp to the entry of accelerometer sensor data corresponding to the determined universal time.

Other embodiments may rely on different formulas for determining the universal time stamp for the entry of accelerometer sensor data. For example, the telematics device may select an entry of GNSS sensor data for use as a reference point. The telematics device may reference the corresponding universal time stamp and local time stamp of the entry of GNSS sensor data. In some embodiments, the telematics device may subtract the time shift from the value of the local time stamp of the entry of GNSS sensor data to determine a corrected local time for the event measured by the entry of GNSS sensor data. The result of the subtraction may provide the approximate local time of the event measured by the universal time stamp in the GNSS sensor data to within an error about equal to or less than the accelerometer sensor integration time. According to various embodiments, for any given entry of accelerometer sensor data, the difference between the value of the entry of accelerometer sensor data and the corrected local time of the entry of GNSS sensor data may be determined, the difference may be converted to universal time units, and the value of the universal time stamp of the entry of GNSS sensor data may be adjusted by the converted difference to determine the universal time corresponding to the event measured by the entry of accelerometer sensor data. It should be understood that other variations of the above methods for determining the universal time corresponding to the event measured by the entry of accelerometer sensor data may also be used.

In various embodiments, the universal time stamp may be determined and assigned to the accelerometer sensor data as it is recorded by the telematics device, for example in real time. Alternatively, the universal time stamp for accelerometer sensor data may not be determined in real time, that is, it may be determined at a time after the recordation of the accelerometer sensor data by the telematics device. In some of these embodiments, a universal time stamp may only be determined for a desired subset of the accelerometer sensor data, such as only for accelerometer sensor data relevant to a particular accident reconstruction. For example, the universal time stamp may only be determined for accelerometer sensor data related to a particular event of interest, such as an accident.

According to certain embodiments, the various delays described above (such as speed of PVT computation, delay due to serial port scheduling, and data buffering at the telematics device) may change depending on conditions present at the time of the measurement and recordation. According to some embodiments, one or more conditions present at the time of sensor data recording may also be recorded. For example, at the time of recording sensor data, the telematics device may also record the processor load and/or temperature, the buffer size of the serial communications port, the buffer size at the telematics device, and the like.

According to various embodiments, one or more of operations 400 through 460 may be repeated over time to determine one or more additional time shift values. Due at least in part to changes in the various delays and present conditions, time drift of the processor clock, or equipment wear, the time shift may change over time. Accordingly, the telematics device may determine a new time shift at various intervals according to one or more of the embodiments described above. In certain embodiments, the telematics device may replace an old time shift value with a new time shift value. In alternative embodiments, the telematics device may maintain more than one time shift value. The one or more time shift values may be used to determine an appropriate time shift value to use when calculating the universal time stamp for accelerometer sensor data. For example, the telematics device may determine an average of the one or more time shifts to use as the time shift value in the calculations. Alternatively, in some embodiments where condition information is recorded, a time shift value corresponding to a time having similar conditions to those of the entry of accelerometer sensor data for which a universal time is being determined may be selected. In certain embodiments where the universal time stamp for accelerometer sensor data is not determined in real time, a time shift value temporally proximate the recorded entry of accelerometer sensor data may be selected.

The following provides an example embodiment of the present invention using example data values. This should be considered a non-limiting, illustrative example of the present invention. Assume that a first event occurs at 01:00:00.000 in universal time, a time that corresponds to a processor clock time of 5000. Additionally, assume that a second event occurs at 01:00:21.350 in universal time, a time that corresponds to a processor clock time of 26350. Assume further that the maximum accelerometer sensor delay is 50 milliseconds, or 00:00:00.050. Note that this accelerometer sensor delay may vary over time. Therefore, in this example, the accelerometer sensor delay may vary anywhere from 0 to 50 milliseconds. Finally, assume that one processor tick equals one millisecond in universal time units, or 00:00:00.001.

A GNSS sensor may measure data over a period of time and provide the data to a telematics device. For the first event, the corresponding entry of GNSS sensor data may contain the universal time of the actual time of the event, or 01:00:00.000. Due to various delays, this entry of GNSS sensor data may not be recorded by the telematics device, however, until a processor clock time of 5750. Therefore, that the delay between the time the event occurs (5000) and the time the entry of GNSS sensor data measuring the event is recorded (5750) is 750 processor clock ticks (5750−5000=750), or 00:00:00.750 in universal time units.

Similarly, an accelerometer sensor may measure data over a period of time and provide the data to the telematics device. For the first event, the corresponding entry of accelerometer sensor data may have an unknown universal time, X. Due to accelerometer sensor delay, this entry of accelerometer sensor data may not be recorded by the telematics device until a processor clock time of 5050. Therefore, the delay between the time the event occurs (5000) and the time the entry of accelerometer sensor data measuring the event is recorded (5050) is 50 processor clock ticks (5050−5000=50), or 00:00:00.050 in universal time units. Note that the delay is equal to the maximum possible accelerometer delay allowable in this example, namely 50 milliseconds or 00:00:00.050.

After performing operations 420 to 450, the telematics device may correlate the time sequence of the GNSS sensor data with the time sequence of the accelerometer sensor data. Accordingly, the correlation may result in determining a time shift of 700 processor clock ticks between the two time sequences. That is, for a given event such as the first event, the time shift may be equal to the difference in the time the corresponding entry of GNSS sensor data was recorded by the telematics device (5750) and the time the corresponding entry of accelerometer sensor data was recorded by the telematics device (5050), namely 700 processor clock ticks (5750−5050=700) or 00:00:00.700.

According to this example, an entry of accelerometer sensor data may be received for the second event at processor clock time 26370, and the universal time of the entry of accelerometer sensor data measuring the second event may be unknown. The universal time of the entry of accelerometer sensor data corresponding to the second event may be determined to within an error less than or equal to the maximum accelerometer sensor delay, however, based at least in part on a reference entry of GNSS sensor data and the time shift. For this example, the reference entry of GNSS sensor data may be the entry of GNSS sensor data corresponding to the first event, thus having a local processor time of 5750 and a universal time of 01:00:00.000. As noted above, in this example the time shift may equal 700 processor clock ticks.

To determine the universal time of the entry of accelerometer sensor data corresponding to the second event, the telematics device may add the time shift (700) to the local processor time that the entry of accelerometer sensor data was received by the telematics device (26370) and subtract the local processor time of the reference entry of GNSS sensor data (5750). The result of this determination provides the approximate time that has elapsed since the reference event, the first event, in processor clock ticks, namely 21320 (700+26370−5750=21320). This result may be converted into universal time units. As noted above, in this example, a processor clock tick may equal 1 millisecond. Therefore, 21320 clock ticks equal 21320 milliseconds, or 00:00:21.320 seconds in universal time units. The result in universal time units (00:00:21.320) may then be added to the universal time of the reference entry of GNSS sensor data (01:00:00.000) to determine the universal time of the entry of accelerometer sensor data corresponding to the second event, or 01:00:21.320 (01:00:00.000+00:00:21.320=01:00:21.320).

As noted above, in this example, the actual universal time of the second event may have been 01:00:21.350. Therefore, the determined universal time of 01:00:21.320 may include an error of 00:00:00.030, or 30 milliseconds. This error may be due to the fact that the accelerometer sensor delay experienced when measuring the first event was different from the accelerometer sensor delay experienced when measuring the second event. In this example, the accelerometer sensor delay for the first event was 50 milliseconds, and the accelerometer sensor delay for the second event was 20 milliseconds. Thus, the overall error in determining the universal time for the accelerometer sensor data of the second event may be equal to the difference between the accelerometer sensor delay for the first event (50 milliseconds) and the second event (20 milliseconds), or, in this example, 30 milliseconds. Accordingly, the error of the determined universal time for the accelerometer sensor data of the second event may be less than or equal to the maximum accelerometer sensor delay.

As described in further detail above, FIG. 4 is a flowchart of a system, method, and computer program product according to example embodiments of the invention. It will be understood that each block or step of the flowchart, and combinations of blocks in the flowchart, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) that embodies the procedures described herein may be stored by one or more memory devices of a terminal, server, or other computing device (e.g., the terminal apparatus 202) and executed by a processor (e.g., the processor 220) in the computing device. In some embodiments, the computer program instructions comprising the computer program product(s) that embodies the procedures described above may be stored by memory devices of a plurality of computing devices. As will be appreciated, any such computer program product may be loaded onto a computer or other programmable apparatus to produce a machine, such that the computer program product including the instructions which execute on the computer or other programmable apparatus creates means for implementing the functions specified in the flowchart block(s) or step(s). Further, the computer program product may comprise one or more computer-readable memories on which the computer program instructions may be stored such that the one or more computer-readable memories can direct a computer or other programmable apparatus to function in a particular manner, such that the computer program product comprises an article of manufacture which implements the function specified in the flowchart block(s) or step(s). The computer program instructions of one or more computer program products may also be loaded onto a computer or other programmable apparatus to cause a series of operational steps to be performed on the computer or other programmable apparatus to produce a computer-implemented process such that the instructions which execute on the computer or other programmable apparatus provide steps for implementing the functions specified in the flowchart block(s) or step(s).

Accordingly, blocks or steps of the flowchart support combinations of means for performing the specified functions and combinations of steps for performing the specified functions. It will also be understood that one or more blocks or steps of the flowchart, and combinations of blocks or steps in the flowchart, may be implemented by special purpose hardware-based computer systems which perform the specified functions or steps, or combinations of special purpose hardware and computer program product(s).

The above described functions may be carried out in many ways. For example, any suitable means for carrying out each of the functions described above may be employed to carry out embodiments of the invention. In one embodiment, a suitably configured processor may provide all or a portion of the elements of the invention. In another embodiment, all or a portion of the elements of the invention may be configured by and operate under control of a computer program product. The computer program product for performing the methods of embodiments of the invention may include a tangible computer-readable storage medium, such as the non-volatile storage medium, and computer-readable program code portions, such as a series of computer instructions, embodied in the computer-readable storage medium.

As such, then, some embodiments of the invention provide several advantages to computing devices and computing device users. Embodiments of the invention provide for synchronizing data across multiple sensors. In this regard, embodiments of the invention provide a telematics device with the capability to associate a universal time stamp with received sensor data that otherwise does not include a universal time stamp. Embodiments of the invention, therefore, allow a telematics device to avoid relying on a non-universal, local time stamp associated with sensor data, which may suffer from error due to significant delays between the time the data is measured and the time the local time stamp is assigned. Embodiments of the invention advantageously provide a universal time stamp for all received sensor data so that data from separate sensors may be synchronized and compared to each other. Furthermore, embodiments of the invention allow received sensor data to be synchronized and coordinated with other external data that is also time stamped based on the same universal time source. Accordingly, embodiments of the present invention may improve the ability of a telematics device to analyze driver behavior and conduct accident reconstruction. Embodiments of the present invention may provide all of this functionality without requiring each sensor to synchronize with or maintain its own reference to a universal time source.

The following provides additional example embodiments of the present invention. One example method in accordance with the invention comprises recording first sensor data provided by at least one first sensor, wherein the first sensor data comprises a universal time stamp based on a universal time source; recording second sensor data provided by at least one second sensor, wherein the second sensor data does not comprise a universal time stamp based on a universal time source; correlating the first sensor data with the second sensor data; and associating the universal time stamp of the first sensor data with the second sensor data that corresponds to the first sensor data, based at least in part on the correlation. According to some example embodiments, the method may further comprise interpolating the first sensor data to generate additional first sensor data such that the time step of the first sensor data equals the time step of the second sensor data. Further, according to some example embodiments, the method may additionally comprise determining the orientation of the at least one second sensor; and adjusting the second sensor data based at least in part on the determined orientation. According to example embodiments, the method may further comprise converting the first sensor data from a first coordinate system associated with the first sensor data to a second coordinate system associated with the second sensor data. Further, according to some example embodiments, the method may additionally comprise integrating the first sensor data to convert the first sensor data from a first value measured by the at least one first sensor to a second value measured by the at least one second sensor.

The following is provided as an example use of an embodiment of the present invention. This should be considered a non-limiting, illustrative example use of the present invention. A user may wish to perform accident reconstruction for insurance purposes related to an accident between three vehicles (e.g. V1, V2, and V3) each having a telematics device (e.g. T1, T2, and T3), a corresponding GNSS sensor (e.g. G1, G2, and G3), and an accelerometer sensor (e.g. A1, A2, and A3), as described in various embodiments above. In the example accident, vehicle V1 may have collided into the back of vehicle V2 causing vehicle V2 to shortly thereafter collide into the back of vehicle V3. The point of the accident reconstruction may be to determine who is liable to vehicle V3. That is, did V2 collide with V3 before V1 collided with V2, which may lead to V2 being held liable, or did V1 collide with V2 before V2 collided with V3, which may lead to V1 being held liable.

In this example, it may be assumed that the zero times of the internal clock of the processor of telematics devices T1, T2, and T3 are not synchronized. That is to say, at any given point in time, the processor clock of each telematics device T1, T2, and T3 reads a different value. Accordingly, the processor times from one vehicle may not be compared to the processor times of another vehicle with any accuracy. Therefore, it would be helpful for all sensor data from each vehicle to have an associated universal time stamp. A common approach to associating a universal time stamp with all sensor data would be to rely on the universal time stamp related to the actual occurrence of the event for which the data measures provided by the GNSS sensors G1, G2, and G3. That is, the telematics devices T1, T2, and T3 may link the universal time stamp contained within the data from G1, G2, and G3 with the processor time at which it is received. As noted above, however, a potential delay of a half second to a full second or more may exist between the time the universal time stamp is stored and the time the GNSS sensor data is received by the telematics device. Furthermore, the processor time of the accelerometer sensor data is only delayed by approximately 20 to 50 milliseconds. Thus, if a universal time having a half to one second delay is assigned to the accelerometer sensor data based on the processor time stamp of the accelerometer sensor data, it may appear that the events corresponding to the accelerometer sensor data occurred before they actually did.

In the example, if the actual time difference between the collision between V1 and V2 and the collision between V2 and V3 is on the order of tenths or hundredths of a second, the half second to one second delay inherent using the common approach discussed above may lead to the incorrect liability determination. That is, it may appear that V2 hit V3 first when in fact V1 hit V2 first. By taking an approach according to various embodiments of the present invention, this error can be reduced to the 20 to 50 millisecond delay of the accelerometer sensor. Accordingly, such an error may be small enough so as not to affect the liability determination. Furthermore, the data from accelerometers A1, A2, and A3 may all be tagged with universal times having the same minimal error of 20 to 50 milliseconds. These highly accurate universal times will further allow data from any sensor from any vehicle to be compared to each other, as all sensor data will have universal time stamps of high accuracy. Therefore, this example demonstrates the usefulness of various embodiments of the present invention.

A related example apparatus for performing data synchronization across multiple sensors comprises at least one processor and at least one memory including computer program code, the at least one memory and the computer program code configured to, with the at least one processor, cause the apparatus at least to perform various functionalities. In this regard, the example apparatus is caused to record first sensor data provided by at least one first sensor, wherein the first sensor data comprises a universal time stamp based on a universal time source; record second sensor data provided by at least one second sensor, wherein the second sensor data does not comprise a universal time stamp based on a universal time source; correlate the first sensor data with the second sensor data; and determine the universal time for an entry of second sensor data, based at least in part on the correlation. According to some example embodiments, the apparatus may be further caused to interpolate the first sensor data to generate additional first sensor data such that the time step of the first sensor data equals the time step of the second sensor data. Further, according to some example embodiments, the apparatus may be additionally caused to determine the orientation of the at least one second sensor; and adjust the second sensor data based at least in part on the determined orientation. According to example embodiments, the apparatus may be further caused to convert the first sensor data from a first coordinate system associated with the first sensor data to a second coordinate system associated with the second sensor data. Further, according to some example embodiments, the apparatus may be additionally caused to integrate the first sensor data to convert the first sensor data from a first value measured by the at least one first sensor to a second value measured by the at least one second sensor.

Another example embodiment is an example computer-readable storage medium having executable computer-readable program code instructions stored therein. The computer-readable program code instructions of the example computer-readable storage medium are for causing an apparatus to perform various functionalities. In this regard, the example apparatus is caused to record first sensor data provided by at least one first sensor, wherein the first sensor data comprises a universal time stamp based on a universal time source; record second sensor data provided by at least one second sensor, wherein the second sensor data does not comprise a universal time stamp based on a universal time source; correlate the first sensor data with the second sensor data; and determine the universal time for an entry of second sensor data, based at least in part on the correlation. According to some example embodiments, the apparatus may be further caused to interpolate the first sensor data to generate additional first sensor data such that the time step of the first sensor data equals the time step of the second sensor data. Further, according to some example embodiments, the apparatus may be additionally caused to determine the orientation of the at least one second sensor; and adjust the second sensor data based at least in part on the determined orientation. According to example embodiments, the apparatus may be further caused to convert the first sensor data from a first coordinate system associated with the first sensor data to a second coordinate system associated with the second sensor data. Further, according to some example embodiments, the apparatus may be additionally caused to integrate the first sensor data to convert the first sensor data from a first value measured by the at least one first sensor to a second value measured by the at least one second sensor.

Another example embodiment is an example apparatus for performing data synchronization across multiple sensors. The example apparatus comprises means for recording first sensor data provided by at least one first sensor, wherein the first sensor data comprises a universal time stamp based on a universal time source; recording second sensor data provided by at least one second sensor, wherein the second sensor data does not comprise a universal time stamp based on a universal time source; correlating the first sensor data with the second sensor data; and determining the universal time for an entry of second sensor data, based at least in part on the correlation. According to some example embodiments, the example apparatus further comprises means for interpolating the first sensor data to generate additional first sensor data such that the time step of the first sensor data equals the time step of the second sensor data. Further, according to some example embodiments, the example apparatus additionally comprises means for determining the orientation of the at least one second sensor; and adjusting the second sensor data based at least in part on the determined orientation. According to example embodiments, the example apparatus further comprises means for converting the first sensor data from a first coordinate system associated with the first sensor data to a second coordinate system associated with the second sensor data. Further, according to some example embodiments, the example apparatus additionally comprises means for integrating the first sensor data to convert the first sensor data from a first value measured by the at least one first sensor to a second value measured by the at least one second sensor.

Many modifications and other embodiments of the inventions set forth herein will come to mind to one skilled in the art to which these inventions pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

The invention claimed is:

1. A method of synchronizing data of at least one first vehicle sensor of a vehicle with data of at least one second vehicle sensor of the vehicle comprising:
    recording, by a vehicle telematics device positioned in the vehicle and comprising one or more processors and one or more memory storage areas operatively connected to the one or more processors, first vehicle sensor data provided by the at least one first vehicle sensor operatively connected to the vehicle telematics device, wherein (a) the first vehicle sensor data comprises (i) a local time stamp based on a local time source indicating the time at which the first vehicle sensor data was recorded by the telematics device, (ii) a universal time stamp based on a universal time source indicating the time at which the first vehicle sensor data was measured by the at least one first vehicle sensor, (b) the at least one first vehicle sensor is synchronized to the universal time source, (c) the universal time source comprises a global navigation satellite system, (d) the local time stamp indicating the time at which the first vehicle sensor data was recorded by the telematics device comprises a delay from the universal time stamp indicating the time at which the first vehicle sensor data was measured by the at least one first vehicle sensor, and (e) the delay comprises at least one of a clock delay, a propagation delay, a computational delay, a buffering delay, a scheduling delay, a drift delay, and a processing delay;
    recording, by the vehicle telematics device positioned in the vehicle, second vehicle sensor data provided by the at least one second vehicle sensor operatively connected to the vehicle telematics device, wherein the second vehicle sensor data comprises (a) a local time stamp based on the local time source indicating the time at which the second vehicle sensor data was recorded by the telematics device but (b) does not comprise a universal time stamp based on the universal time source indicating the time at which the second vehicle sensor data was measured by the at least one second vehicle sensor;
    interpolating the first vehicle sensor data to generate additional first vehicle sensor data such that a time step of the first vehicle sensor data equals a time step of the second vehicle sensor data;
    determining an orientation of the at least one second vehicle sensor;
    adjusting the second vehicle sensor data based at least in part on the determined orientation;
    converting the first vehicle sensor data from a first coordinate system associated with the first vehicle sensor data to a second coordinate system associated with the second vehicle sensor data based at least in part on the adjusted second vehicle sensor data;
    transforming the first vehicle sensor data to convert the first vehicle sensor data from a first value measured by the at least one first vehicle sensor to a second value corresponding to a type of data measured by the at least one second vehicle sensor;
    determining a time shift, by the vehicle telematics device positioned in the vehicle, between the first vehicle sensor data and the second vehicle sensor data by performing cross-correlation between the second vehicle sensor data and the first vehicle sensor data, wherein the first vehicle sensor data (1) has been converted to the second coordinate system associated with the second vehicle sensor data and (2) has been transformed to the second value corresponding to the type of data measured by the at least one second vehicle sensor;
    in response to determining the time shift between the first vehicle sensor data and the second vehicle sensor data, synchronizing the first vehicle sensor data with the second vehicle sensor data by determining a universal time that corresponds to the second vehicle sensor data based at least in part on (a) the universal time stamp of the first vehicle sensor data, and (b) the time shift determined from the cross-correlation between the first vehicle sensor data and the second vehicle sensor data; and in response to determining the universal time, recording, by the vehicle telematics device positioned in the vehicle, new first vehicle sensor data and new second vehicle sensor data, wherein the new first vehicle sensor data and second vehicle sensor data are each recorded in real time in association with the determined universal time based on the synchronization.

2. The method of claim 1 further comprising:
associating a universal time stamp corresponding to the determined universal time with the second vehicle sensor data.

3. The method of claim 1, wherein interpolating is selected from the group consisting of spline interpolation, linear interpolation, and polynomial interpolation.

4. A vehicle telematics device positioned in a vehicle and comprising at least one processor and at least one memory including computer program code, the at least one memory and the computer program code configured to, with the processor, cause the vehicle telematics device to at least:
record first vehicle sensor data provided by at least one first vehicle sensor operatively connected to the vehicle telematics device, wherein (a) the first vehicle sensor data comprises (i) a local time stamp based on a local time source indicating the time at which the first vehicle sensor data was recorded by the telematics device, (ii) a universal time stamp based on a universal time source indicating the time at which the first vehicle sensor data was measured by the at least one first vehicle sensor, (b) the at least one first vehicle sensor is synchronized to the universal time source, (c) the universal time source comprises a global navigation satellite system, (d) the local time stamp indicating the time at which the first vehicle sensor data was recorded by the telematics device comprises a delay from the universal time stamp indicating the time at which the first vehicle sensor data was measured by the at least one first vehicle sensor, and (e) the delay comprises at least one of a clock delay, a propagation delay, a computational delay, a buffering delay, a scheduling delay, a drift delay, and a processing delay;
record second vehicle sensor data provided by at least one second vehicle sensor operatively connected to the vehicle telematics device, wherein the second vehicle sensor data comprises (a) a local time stamp based on the local time source indicating the time at which the second vehicle sensor data was recorded by the telematics device but (b) does not comprise a universal time stamp based on the universal time source indicating the time at which the second vehicle sensor data was measured by the at least one second vehicle sensor;
interpolate the first vehicle sensor data to generate additional first vehicle sensor data such that a time step of the first vehicle sensor data equals a time step of the second vehicle sensor data;
determine an orientation of the at least one second vehicle sensor;
adjust the second vehicle sensor data based at least in part on the determined orientation;
convert the first vehicle sensor data from a first coordinate system associated with the first vehicle sensor data to a second coordinate system associated with the second vehicle sensor data based at least in part on the adjusted second vehicle sensor data;
transform the first vehicle sensor data to convert the first vehicle sensor data from a first value measured by the at least one first vehicle sensor to a second value corresponding to a type of data measured by the at least one second vehicle sensor;
determine a time shift between the first vehicle sensor data and the second vehicle sensor data by performing cross-correlation between the second vehicle sensor data and the first vehicle sensor data, wherein the first vehicle sensor data (1) has been converted to the second coordinate system associated with the second vehicle sensor data and (2) has been transformed to the second value corresponding to the type of data measured by the at least one second vehicle sensor;
in response to determining the time shift between the first vehicle sensor data and the second vehicle sensor data, synchronize the first vehicle sensor data with the second vehicle sensor data by determining a universal time that corresponds to the second vehicle sensor data based at least in part on (a) the universal time stamp of the first vehicle sensor data, and (b) the time shift determined from the cross-correlation between the first vehicle sensor data and the second vehicle sensor data; and
in response to determining the universal time, record new first vehicle sensor data and new second vehicle sensor data, wherein the new first vehicle sensor data and second vehicle sensor data are each recorded in real time in association with the determined universal time based on the synchronization.

5. The vehicle telematics device of claim 4, wherein the memory and computer program code are further configured to, with the processor, cause the apparatus to at least:
associate a universal time stamp corresponding to the determined universal time with the second vehicle sensor data.

6. The vehicle telematics device of claim 4, wherein interpolating is selected from the group consisting of spline interpolation, linear interpolation, and polynomial interpolation.

7. A computer program product for synchronizing data of at least one first vehicle sensor of a vehicle with data of at least one second vehicle sensor of the vehicle, the computer program product comprising at least one non-transitory computer-readable storage medium having computer-readable program code portions stored therein, the computer-readable program code portions comprising:
an executable portion configured to record, by a vehicle telematics device positioned in the vehicle and comprising one or more processors and one or more memory storage areas operatively connected to the one or more processors, first vehicle sensor data provided by the at least one first vehicle sensor operatively connected to the vehicle telematics device, wherein (a) the first vehicle sensor data comprises (i) a local time stamp based on a local time source indicating the time at which the first vehicle sensor data was recorded by the telematics device, (ii) a universal time stamp based on a universal time source indicating the time at which the first vehicle sensor data was measured by the at least one first vehicle sensor, (b) the at least one first vehicle sensor is synchronized to the universal time source, (c) the universal time source comprises a global navigation satellite system, (d) the local time stamp indicating the time at which the first vehicle sensor data was recorded by the telematics device comprises a delay from the universal time stamp indicating the time at which the first vehicle sensor data was measured by the at least one first vehicle sensor, and (e) the delay comprises at least one of a clock delay, a propagation delay, a computational delay, a buffering delay, a scheduling delay, a drift delay, and a processing delay;

an executable portion configured to record, by the vehicle telematics device positioned in the vehicle, second vehicle sensor data provided by the at least one second vehicle sensor operatively connected to the vehicle telematics device, wherein the second vehicle sensor data comprises (a) a local time stamp based on the local time source indicating the time at which the second vehicle sensor data was recorded by the telematics device but (b) does not comprise a universal time stamp based on the universal time source indicating the time at which the second vehicle sensor data was measured by the at least one second vehicle sensor;

an executable portion configured to interpolate the first vehicle sensor data to generate additional first vehicle sensor data such that a time step of the first vehicle sensor data equals a time step of the second vehicle sensor data;

an executable portion configured to determine an orientation of the at least one second vehicle sensor;

an executable portion configured to adjust the second vehicle sensor data based at least in part on the determined orientation;

an executable portion configured to convert the first vehicle sensor data from a first coordinate system associated with the first vehicle sensor data to a second coordinate system associated with the second vehicle sensor data based at least in part on the adjusted second vehicle sensor data;

an executable portion configured to transform the first vehicle sensor data to convert the first vehicle sensor data from a first value measured by the at least one first vehicle sensor to a second value corresponding to a type of data measured by the at least one second vehicle sensor;

an executable portion configured to determine a time shift, by the vehicle telematics device positioned in the vehicle, between the first vehicle sensor data and the second vehicle sensor data by performing cross-correlation between the second vehicle sensor data and the first vehicle sensor data, wherein the first vehicle sensor data (1) has been converted to the second coordinate system associated with the second vehicle sensor data and (2) has been transformed to the second value corresponding to the type of data measured by the at least one second vehicle sensor;

an executable portion configured to, in response to determining the time shift between the first vehicle sensor data and the second vehicle sensor data synchronize the first vehicle sensor data with the second vehicle sensor data by determining a universal time that corresponds to the second vehicle sensor data based at least in part on (a) the universal time stamp of the first vehicle sensor data, and (b) the time shift determined from the cross-correlation between the first vehicle sensor data and the second vehicle sensor data; and an executable portion configured to, in response to determining the universal time, record, by the vehicle telematics device positioned in the vehicle, new first vehicle sensor data and new second vehicle sensor data, wherein the new first vehicle sensor data and second vehicle sensor data are each recorded in real time and in association with the determined universal time based on the synchronization.

8. The computer program product of claim 7, further comprising:

an executable portion configured to associate a universal time stamp corresponding to the determined universal time with the second vehicle sensor data.

9. The computer program product of claim 7, wherein interpolating is selected from the group consisting of spline interpolation, linear interpolation, and polynomial interpolation.

* * * * *